United States Patent
Wong et al.

(10) Patent No.: US 11,869,151 B2
(45) Date of Patent: Jan. 9, 2024

(54) SYSTEMS AND METHODS FOR FINITE ELEMENT ANALYSIS OF TUMOR TREATING FIELDS

(71) Applicant: Beth Israel Deaconess Medical Center, Boston, MA (US)

(72) Inventors: Eric T. Wong, Milton, MA (US); Edwin Lok, Braintree, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 17/585,187

(22) Filed: Jan. 26, 2022

(65) Prior Publication Data

US 2022/0237871 A1 Jul. 28, 2022

Related U.S. Application Data

(60) Provisional application No. 63/141,832, filed on Jan. 26, 2021.

(51) Int. Cl.
| | |
|---|---|
| *G06T 15/00* | (2011.01) |
| *G06T 17/20* | (2006.01) |
| *G06T 7/10* | (2017.01) |

(52) U.S. Cl.
CPC ............. *G06T 17/20* (2013.01); *G06T 7/10* (2017.01); *G06T 2207/10088* (2013.01);
(Continued)

(58) Field of Classification Search
USPC ........................................... 345/418
See application file for complete search history.

(56) References Cited

U.S. PATENT DOCUMENTS

| | | | |
|---|---|---|---|
| 8,494,627 B2 | 7/2013 | Bikson et al. | |
| 11,077,320 B1 * | 8/2021 | Hibbard | G16H 20/40 |

(Continued)

FOREIGN PATENT DOCUMENTS

| | | |
|---|---|---|
| WO | WO 2010/120823 A2 | 10/2010 |
| WO | WO 2015/142922 A1 | 9/2015 |
| WO | WO 2017/072706 A1 | 5/2017 |

OTHER PUBLICATIONS

Berger TR, Wong ET. Tumor treating fields in neuro-oncology: integration of alternating electric fields therapy into promising treatment strategies. Chin Clin Oncol. Feb. 29, 2020;1:1-2.*

(Continued)

*Primary Examiner* — Phu K Nguyen
(74) *Attorney, Agent, or Firm* — Wolf, Greenfield & Sacks, P.C.

(57) ABSTRACT

Aspects of the technology described herein relate to systems and techniques for finite element analysis of alternating electric fields such as tumor treating fields. A system may be configured to receive medical data of the patient, generate segmented medical data by performing segmentation using the medical data of the patient, generate a model for a transducer array configuration and the generated segmented medical data, wherein the transducer array configuration is configured to produce alternating electric fields, and determine one or more metrics of the alternating electric fields for each of the one or more transducer array configurations. The system may further compare the metrics to reference values and/or metrics of another transducer array configuration and/or determine and/or recommend a transducer array configuration based on the metrics.

20 Claims, 7 Drawing Sheets

(52) U.S. Cl.
CPC ............... *G06T 2207/30016* (2013.01); *G06T 2207/30096* (2013.01); *G06T 2210/41* (2013.01)

(56) References Cited

U.S. PATENT DOCUMENTS

| | | | |
|---|---|---|---|
| 11,154,707 B2* | 10/2021 | Bomzon | G16H 50/50 |
| 11,383,102 B2* | 7/2022 | Moore | G16H 20/40 |
| 11,446,487 B2 | 9/2022 | Wong et al. | |
| 2004/0006373 A1* | 1/2004 | Brighton | A61N 1/326 607/1 |
| 2010/0030211 A1 | 2/2010 | Davalos et al. | |
| 2012/0226200 A1 | 9/2012 | Wagner et al. | |
| 2016/0055304 A1 | 2/2016 | Russell et al. | |
| 2019/0030370 A1* | 1/2019 | Hibbard | A61N 5/1067 |
| 2020/0074315 A1* | 3/2020 | Katz | G06N 5/022 |
| 2020/0353286 A1* | 11/2020 | Wu | A61N 5/1031 |
| 2021/0069527 A1* | 3/2021 | Peltola | A61N 5/1031 |

OTHER PUBLICATIONS

Korshoej AR, Hansen FL, Mikic N, von Oettingen G, Sørensen JC, Thielscher A. Importance of electrode position for the distribution of tumor treating fields (TTFields) in a human brain. Identification of effective layouts through systematic analysis of array positions for multiple tumor locations. PLoS One. 2018 Au.*

Lok E, San P, Liang O, White V, Wong ET. Finite element analysis of Tumor Treating Fields in a patient with posterior fossa glioblastoma. Journal of neuro-oncology. Mar. 2020;147:125-33.*

Aerts S, Deschrijver D, Verloock L, Dhaene T, Martens L, Joseph W. Assessment of outdoor radiofrequency electromagnetic field exposure through hotspot localization using kriging-based sequential sampling. Environmental research. Oct. 1, 2013;126:184-91.*

Laakso I, Hirata A. Reducing the staircasing error in computational dosimetry of low-frequency electromagnetic fields. Physics in medicine & biology. Jan. 31, 2012;57(4):N25.*

Cang H, Labno A, Lu C, Yin X, Liu M, Gladden C, Liu Y, Zhang X. Probing the electromagnetic field of a 15-nanometre hotspot by single molecule imaging. Nature. Jan. 20, 2011;469(7330):385-8.*

Nelms BE, Robinson G, Markham J, Velasco K, Boyd S, Narayan S, Wheeler J, Sobczak ML. Variation in external beam treatment plan quality: an inter-institutional study of planners and planning systems. Practical radiation oncology. Oct. 1, 2012;2(4):296-305.*

International Search Report and Written Opinion for International Application No. PCT/US2017/053051 dated Aug. 20, 2018.

International Preliminary Report on Patentability for International Application No. PCT/US2017/053051 dated Apr. 4, 2019.

[No Author Listed], Food and Drug Administration Neurological Devices Panel. NovoCure Ltd. NovoTTF-100A System. Mar. 17, 2011. 263 pages. https://web.archive.org/web/20170221214539/ Http://Www.Fda.Gov/Ucm/Groups/Fdagov-Public/@Fdagov-Afda-Adcom/Documents/Document/Ucm247168.Pdf [last accessed Jun. 17, 2019 using Internet Archive Wayback Machine].

Gera et al., Tumor treating fields perturb the localization of septins and cause aberrant mitotic exit. PLoS One. May 26, 2015;10(5):e0125269, 23 pages. doi: 10.1371/journal.pone. 0125269.

Gur et al., Gender differences in age effect on brain atrophy measured by magnetic resonance imaging. Proc Natl Acad Sci U S A. Apr. 1, 1991;88(7):2845-9.

Hasgall et al., IT'IS Database for thermal and electromagnetic parameters of biological tissues. Version 4.0. May 15, 2018. doi: 10.13099/VIP21000-04-0. itis.swiss/database. https://itis.swiss/ virtual-population/tissue-properties/overview [last accessed on Jun. 17, 2019].

Hoelscher et al., SELDI-TOF analysis of glioblastoma cyst fluid is an approach for assessing cellular protein expression. Neurol Res. Dec. 2013;35(10):993-1001. doi:10.1179/016164113X13756993777580.

Kirson et al., Alternating electric fields arrest cell proliferation in animal tumor models and human brain tumors. Proceedings of the National Academy of Sciences of the United States of America. 2007;104(24):10152-10157.

Kirson et al., Disruption of cancer cell replication by alternating electric fields. Cancer Res. May 1, 2004;64(9):3288-95.

Lohle et al., Analysis of fluid in cysts accompanying various primary and metastatic brain tumours: proteins, lactate and pH. Acta Neurochir (Wien). 1998;140(1):14-9.

Lok et al., Computed modeling of alternating electric fields therapy for recurrent glioblastoma. Cancer Medicine. Aug. 26, 2015;4(11):1697-9.

Lok et al., Tumor treating fields therapy device for glioblastoma: physics and clinical practice considerations. Expert Rev Med Devices. 2015;12(6):717-26. doi: 10.1586/17434440.2015.1086641.

Miranda et al., Predicting the electric field distribution in the brain for the treatment of glioblastoma. Phys Med Biol. Aug. 7, 2014;59(15):4137-47. doi: 10.1088/0031-9155/59/15/4137.

Stupp et al., Maintenance Therapy With Tumor-Treating Fields Plus Temozolomide vs Temozolomide Alone for Glioblastoma: A Randomized Clinical Trial. JAMA. Dec. 15, 2015;314(23):2535-43. doi: 10.1001/jama.2015.16669.

Stupp et al., NovoTTF-100A versus physician's choice chemotherapy in recurrent glioblastoma: a randomized phase III trial of a novel treatment modality. Eur J Cancer. Sep. 2012;48(14):2192-202. doi: 10.1016/j.ejca.2012.04.011.

Wenger et al., Improving Tumor Treating Fields Treatment Efficacy in Patients With Glioblastoma Using Personalized Array Layouts. Int J Radiat Oncol Biol Phys. Apr. 1, 2016;94(5):1137-43. doi: 10.1016/j.ijrobp.2015.11.042.

Wenger et al., The electric field distribution in the brain during TTFields therapy and its dependence on tissue dielectric properties and anatomy: a computational study. Phys Med Biol. Sep. 21, 2015;60(18):7339-57. doi: 10.1088/0031-9155/60/18/7339.

Wong, Tumor growth, invasion, and angiogenesis in malignant gliomas. J Neurooncol. May 2006;77(3):295-6. doi: 10.1007/s11060-005-9042-8.

* cited by examiner

FIG. 5

SYSTEMS AND METHODS FOR FINITE ELEMENT ANALYSIS OF TUMOR TREATING FIELDS

CROSS-REFERENCE TO RELATED APPLICATIONS

The present application claims the benefit under 35 U.S.C. § 119(e) of U.S. Patent Application Ser. No. 63/141,832, filed Jan. 26, 2021, and entitled "SYSTEMS AND METHODS FOR FINITE ELEMENT ANALYSIS OF TUMOR TREATING FIELDS," which is hereby incorporated by reference herein in its entirety.

FIELD

Generally, the aspects of the technology described herein relate to systems and methods of determining one or more metrics of a transducer array configuration on a user (e.g., patient) using finite element analysis. Certain aspects relate to using the determined one or more metrics to determine an optimal transducer array configuration.

BACKGROUND

Therapy using alternating electric fields (e.g., TTFields therapy) is an accepted treatment modality for cancers such as supratentorial glioblastoma because of its ability to prolong the survival of patients. These electric fields (e.g., TTFields) are delivered to the scalp of a patient via a number of pairs (e.g., 2) of orthogonally positioned transducer arrays and, at a specified frequency (e.g., 200 kHz), these alternating electric fields can penetrate the scalp and calvarium into the intracranial space to produce an antitumor effect by disrupting tumor cell cytokinesis during mitosis and enabling immunogenic cell death.

Patient survival benefit of TTFields has been demonstrated in randomized clinical trials but much of the data are available only for supratentorial glioblastomas.

SUMMARY

According to one aspect of the present application, a method for determining one or more metrics of a transducer array configuration for a patient is provided, the method comprising receiving medical data of the patient, generating segmented medical data by performing segmentation using the medical data of the patient, generating a model for a transducer array configuration and generated segmented medical data, wherein the transducer array configuration is configured to produce alternating electric fields, determining one or more metrics of the alternating electric fields for each of the one or more transducer array configurations.

In some embodiments, the method includes generating an electric field-volume histogram (EVH) and/or a current density volume histogram (CDVH).

In some embodiments, one or more metrics are indicative of strength of the electric fields and current densities of the alternating electric fields.

In some embodiments, the one or more metrics comprises Plan Quality Metrics (PQM).

In some embodiments, the one or more metrics comprises area under the curve in the EVH for electric field ($E_{AUC}$) and/or area under the curve in the CDVH for current density ($CD_{AUC}$).

In some embodiments, the alternating electric fields comprise tumor treating fields (TTfields).

In some embodiments, the alternating electric fields comprise tumor treating fields (TTfields).

In some embodiments, the one or more metrics comprise a median volume for the alternating electric fields covering the GTV and cerebellum.

In some embodiments, the transducer array configuration is a first transducer array configuration of a plurality of transducer array configurations, and wherein the method further comprises comparing the one or more metrics to one or more metrics of other transducer array configurations of the plurality of transducer array configurations.

In some embodiments, the method further comprises recommending, based on comparing the one or more metrics, a recommended transducer array configuration.

In some embodiments, the one or more metrics comprises average electric field hotspot.

In some embodiments, the model comprises a three-dimensional finite-element mesh.

In some embodiments, the determining one or more metrics comprises performing finite element analysis.

In some embodiments, performing segmentation comprises segmenting neuro-anatomical structures.

In some embodiments, the medical data includes T1 and/or T2 MRI sequences.

Some aspects of the present application include a system, comprising at least one computer hardware processor and at least one non-transitory computer-readable storage medium storing processor-executable instructions that, when executed by at least one processor, cause the at least one processor to perform the above aspects and embodiments.

Some aspects of the present application include at least one non-transitory computer-readable storage medium storing processor-executable instructions that, when executed by at least one processor, cause the at least one processor to perform the above aspects and embodiments. Some aspects include an apparatus having a processing device configured to perform the above aspects and embodiments.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

FIG. 5 is a table illustrating values of metrics from performing finite element analysis, in accordance with certain embodiments described herein.

DETAILED DESCRIPTION

Figure 1:
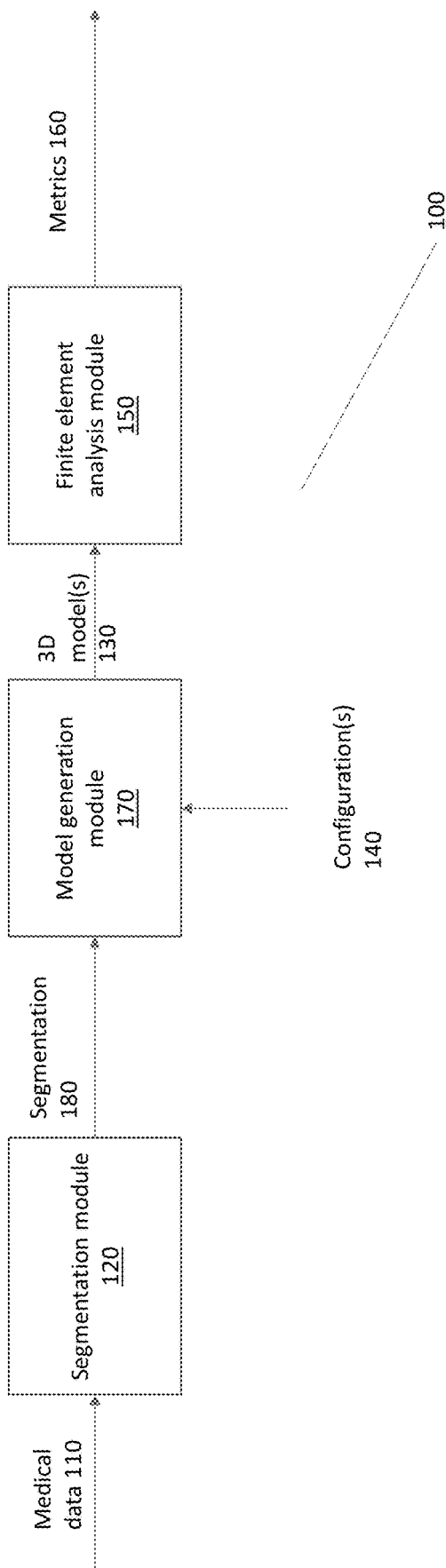
FIG. 1 illustrates a system for finite element analysis of tumor treating fields, in accordance with certain embodiments described herein.

Therapy using alternating electric fields (e.g., TTFields therapy) is an accepted treatment modality for cancers due to its ability to prolong the survival of patients. These electric fields are delivered to the scalp of a patient via pairs of orthogonally positioned transducer arrays. The orthogonally positioned transducer arrays deliver the alternating electric fields at a specified frequency (e.g., 200 kHz), which may penetrate the scalp and calvarium into the intracranial space to produce an antitumor effect by disrupting tumor cell cytokinesis during mitosis and enabling immunogenic cell death.

When applied to newly diagnosed glioblastoma patients in a randomized clinical trial, those who received TTFields and adjuvant temozolomide had an improved overall survival of 20.9 months compared to the 16.0 months in the control cohort treated with adjuvant temozolomide alone. The median progression-free survival was also prolonged to 6.7 months from 4.0 months. A unique adverse event related to TTFields is the mild to moderate scalp irritation at the sites of array application. Collectively, these data indicate that TTFields offer substantial clinical benefit to glioblastoma patients with acceptable toxicity.

A standard placement of the transducer arrays is designed for the delivery of TTFields to tumors located in the supratentorial brain. But there is substantial variability among patients with respect to the intracranial distribution of TTFields and, depending on the array layouts, the electric field coverage at the gross tumor volume (GTV) can vary up to 23% according to a computer simulation study. For tumors in the posterior fossa, the standard array configuration appears to provide minimal electric field coverage and there is no accepted array placement for this location.

The inventors have realized that using methods of performing finite element analysis to determine one or more metrics associated with alternating electric fields produced by one or more transducer array configuration on a user (e.g., patient) can be used to determine a recommended transducer array configuration, for example, that is more effective than the standard placement. For example, performing finite element computer simulations of a patient (e.g., with cerebellar glioblastoma undergoing TTFields treatment) using different array configurations, can help determine metrics indicative of coverage and intensity of the electric fields (e.g., TTfields) configured to be produced by the different transducer array configurations.

According to some embodiments, the metrics can include Plan Quality Metrics (PQM) derived from generated electric field-volume histogram (EVH) and current density volume histogram (CDVH). According to some embodiments, the overall field coverage of the GTV and the cerebellum among various array placements were also compared using the metrics of the area under the curve in the EVH ($E_{AUC}$) and in the CDVH ($CD_{AUC}$) for electric field and current density, respectively.

A method may include receiving medical data of the patient, generating segmented medical data by performing segmentation using the medical data of the patient, generating a model for a transducer array configuration and generated segmented medical data, wherein the transducer array configuration is configured to produce alternating electric fields, determining one or more metrics of the alternating electric fields for each of the one or more transducer array configurations.

For example, in one configuration, the posteroanterior (PA) array is shifted downward to the lower occipital and upper cervical regions and the right and left lateral arrays are moved backward. One simulation demonstrated that this posterior fossa configuration significantly increased the electric field coverage to the cerebellar GTV, as measured by the area under the curve (AUC) of the electric field-volume histogram (EVH). In addition, the modified array configuration produces hotspots proportional to TTFields coverage at the cerebellar GTV.

FIG. 1 is a diagram of an illustrative system 100 for performing finite element analysis of tumor treating fields, in accordance with certain embodiments described herein.

The system 100 include a segmentation module 120 configured to access or receive medical data 110. The segmentation module 120 may be configured to output a three-dimensional (3D) model 130, such as a three-dimensional finite-element mesh. The system may also include a finite element analysis module 150 which takes in both the 3D model 130 and one or more potential transducer array configurations 140. For each of the one or more transducer array configurations, the finite element analysis module 150 may perform one or multiple operations in order to calculate metrics, such as metrics 160, which may include metrics associated with the alternating electric fields produced by the transducer array configuration.

According to some embodiments, the medical data 110 may include any relevant data such as MRI sequences (e.g., T1 and T2), MP RAGE sequences, and/or the like. In some embodiments, the medical data 110 may be stored in a database and/or as one or multiple files and may be provided to the segmentation module 120 (e.g., a user or another system/module may input the medical data into the system). For example, the medical data 110, or a file or data structure including the medical data, may be uploaded to the module 120. Alternatively, the system may be configured to access the medical data through a request.

In the example provided in FIGS. 2-5, MP RAGE, T1 and T2 MRI sequences from a 63-year-old woman with a glioblastoma located in the posterior fossa were used to perform finite element analysis.

According to some embodiments, the system 100 may be configured to use the medical data 110 and perform segmentation using segmentation module 120. Segmentation module 120 is configured to segment structures including neuro-anatomical structures (e.g., semi-automatically, automatically, etc.) depicted in the medical data 110, using methods previously described. For example, various intracranial structures can be imported into segmentation module 120 (e.g., a software or application such as Simpleware (Exeter, UK)) where unspecified and unsegmented structures, such as muscles, blood vessels, parotid glands, vertebral body, mandible, tongue, epidural tissues, GTV and necrotic core(s) within the GTV can be delineated. In some embodiments, an additional step may be included such that after the segmentation was completed by segmentation module 120, the system may prompt a user, such as a neuro-oncologist, to review and/or confirm the accuracy of the 3D model.

The segmentation 180 may be input into model generation module 170. The model generation module 170 may be configured to output a model for each of the one or multiple configurations 140 using the medical data 110 and the corresponding configuration of the configuration(s) 140. According to some embodiments, the 3D model may be a three-dimensional finite-element mesh. The finite element analysis module 150 may use the 3D model, e.g., mesh for finite element analysis (e.g., COMSOL Multiphysics (Burlington, Mass.)) to determine metrics indicative of the effects of alternating electric fields (e.g., TTFields) produced by each of the transducer array configurations 140.

Figure 2:
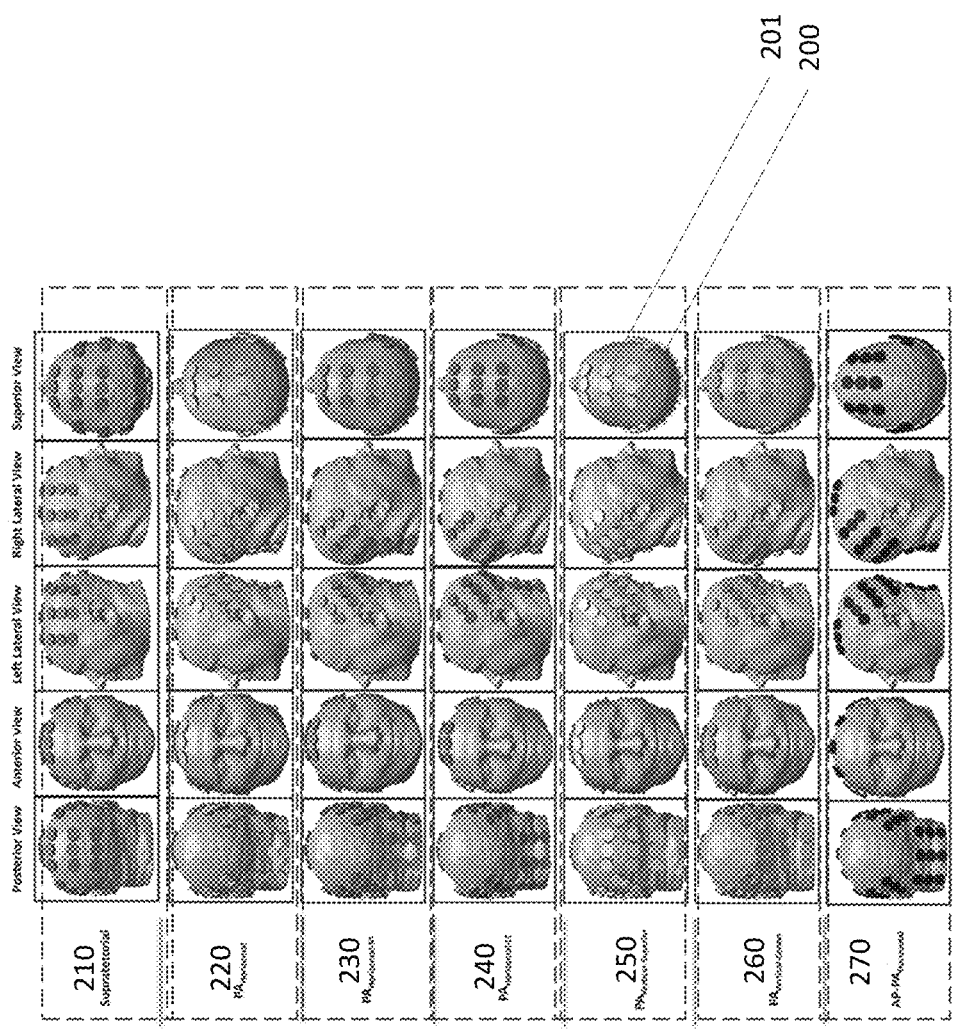
FIG. 2 illustrates various array configuration layouts, in accordance with certain embodiments described herein.

The transducer array configurations may include any configuration of transducer arrays to produce alternating electric fields. For example, FIG. 2 illustrates various array configurations 210, 220, 230, 240, 250, 260 and 270, according to some embodiments. Each of the circular nodes 201 represent a transducer array on the scalp of a patient 200. FIG. 2 shows transducer array configuration 210, representing a supratentorial array configuration. In the example of FIG. 2, the configuration 210 is generated by NovoTAL (a proprietary treatment planning software from Novocure, LTD.).

The configurations 220, 230, 240, 250 and 260 illustrate alternative array configurations developed for tumors within the posterior fossa. In the example of FIG. 2, the configuration 260 denoted $PA_{Vertical-Center}$, one of the posterior fossa array configurations, may be derived from the supratentorial array configuration 210, by shifting the two lateral and the PA arrays from the supratentorial array configuration.

The configurations 220, 230, 240 and 250 may be derived by shifting the PA array (e.g., manually) from the $PA_{Vertical-center}$ position to 5 different positions. The configurations 220, 230, 240, and 250, 270 are denoted as $PA_{Horizontal}$, $PA_{Horizontal-Right}$, $PA_{Horizontal-Left}$, $PA_{Vertical-Superior}$, and $AP-PA_{Horizontal}$, respectively.

Figure 4:
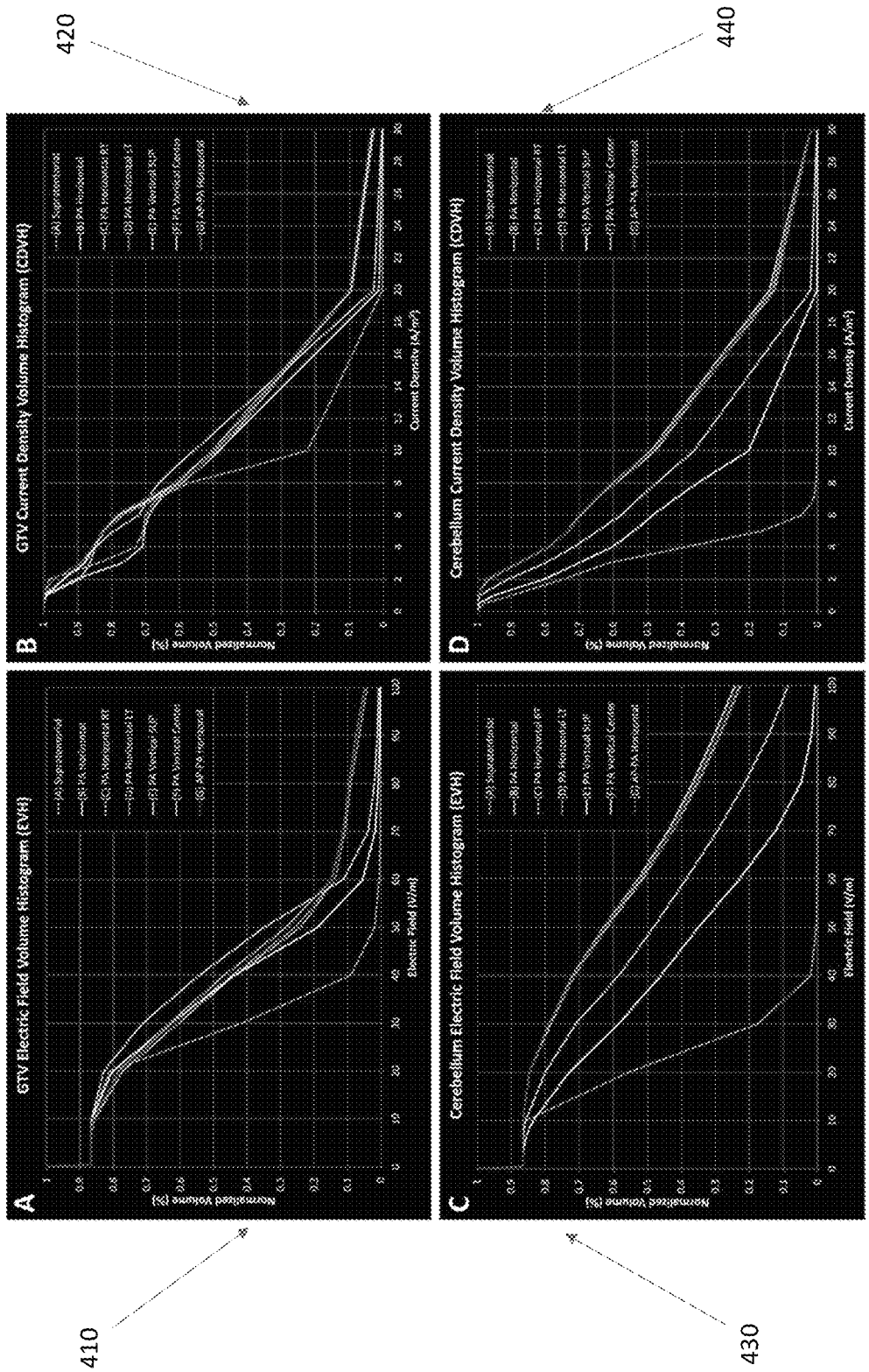
FIG. 4 illustrates electric field-volume histogram (EVH) and SARVH generated from the various array configurations for gross tumor volume (GTV) and cerebellum, in accordance with certain embodiments described herein.

According to some embodiments, in order to provide/calculate metrics to compare TTFields coverage and intensity between models, the finite element analysis module may first generate electric field-volume histogram (EVH) and current density volume histogram (CDVH) using the medical data, the model, the configurations and/or both. For example, FIG. 4 shows exemplary EVH and CDVH histograms, in accordance with some embodiments. Histogram 410 is an exemplary GTV electric field volume histogram (EHV) of the configurations shown in FIG. 2. Histogram 420 is an exemplary GTV current density volume histogram (CDVH) of the configurations shown in FIG. 2. Histogram 430 is an exemplary cerebellum electric field volume histogram (EHV) of the configurations shown in FIG. 2. Histogram 440 is an exemplary cerebellum current density volume histogram (CDVH) of the configurations shown in FIG. 2.

The metrics 160 may include Plan Quality Metrics (PQM), which may be derived from these histograms for the purpose of quantitative comparisons. The overall field coverage of the GTV and the cerebellum among various array placements were also compared using the metrics of the area under the curve in the EVH ($E_{AUC}$) and in the CDVH ($CD_{AUC}$) for electric field and current density, respectively. Another metric may include the median volume for TTFields covering the GTV and cerebellum were also compared between the different array configurations and they are denoted as E50% and CD50%. In order to compare field intensities much higher than what was received by 50% in the region of interest (ROI), these hotspot regions are defined as 5% of the total volume of the ROI and denoted them as E5% and CD5%.

Figure 3:
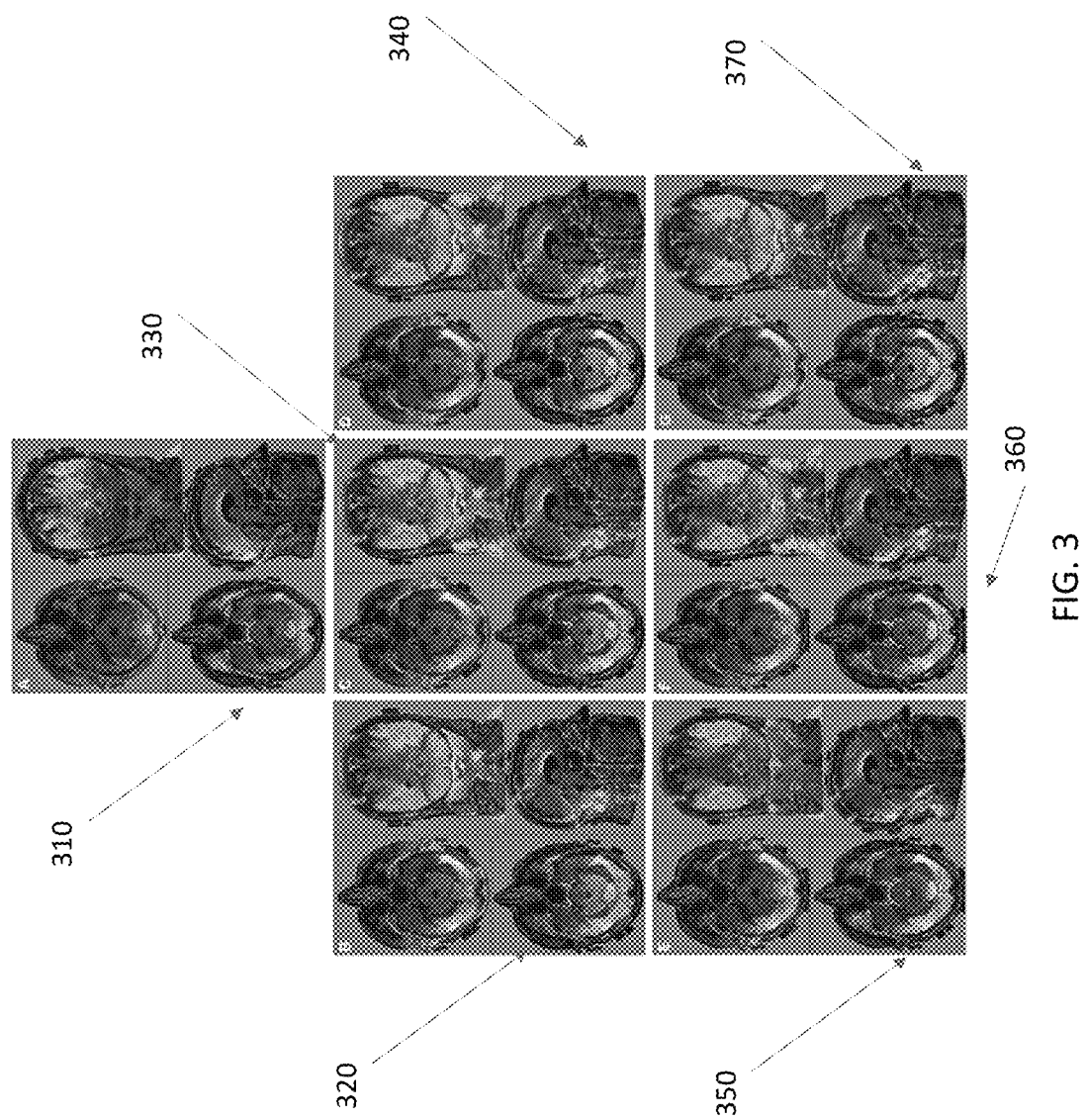
FIG. 3 illustrates electric field and current density distribution overlays, in accordance with certain embodiments described herein.

FIG. 3 shows exemplary electric field and current density distribution overlays. For each of the panels 310, 320, 330, 340, 350, 360, and 370, the upper left corner is an axial plane with electric field overlay, while the lower left corner is an axial plane with current density overlay, the upper right corner in each panel is a coronal plane with the electric field overlay, and the lower right corner is a sagittal plane with the electric field overlay. Panel 310 includes overlays corresponding to the supratentorial array configuration. Panel 320 includes overlays corresponding to the alternative array configuration with PAHorizontal. Panel 330 includes overlays corresponding to the alternative array configuration with PAHorizontal-RT. Panel 340 includes overlays corresponding to the alternative array configuration with PAHorizontal-LT. Panel 350 includes overlays corresponding to the alternative array configuration with PAVertical-Center. Panel 360 includes overlays corresponding to the alternative array configuration with PAVertical-Superior. Panel 370 includes overlays corresponding to the alternative array configuration with AP-PAHorizontal.

Figure 6:
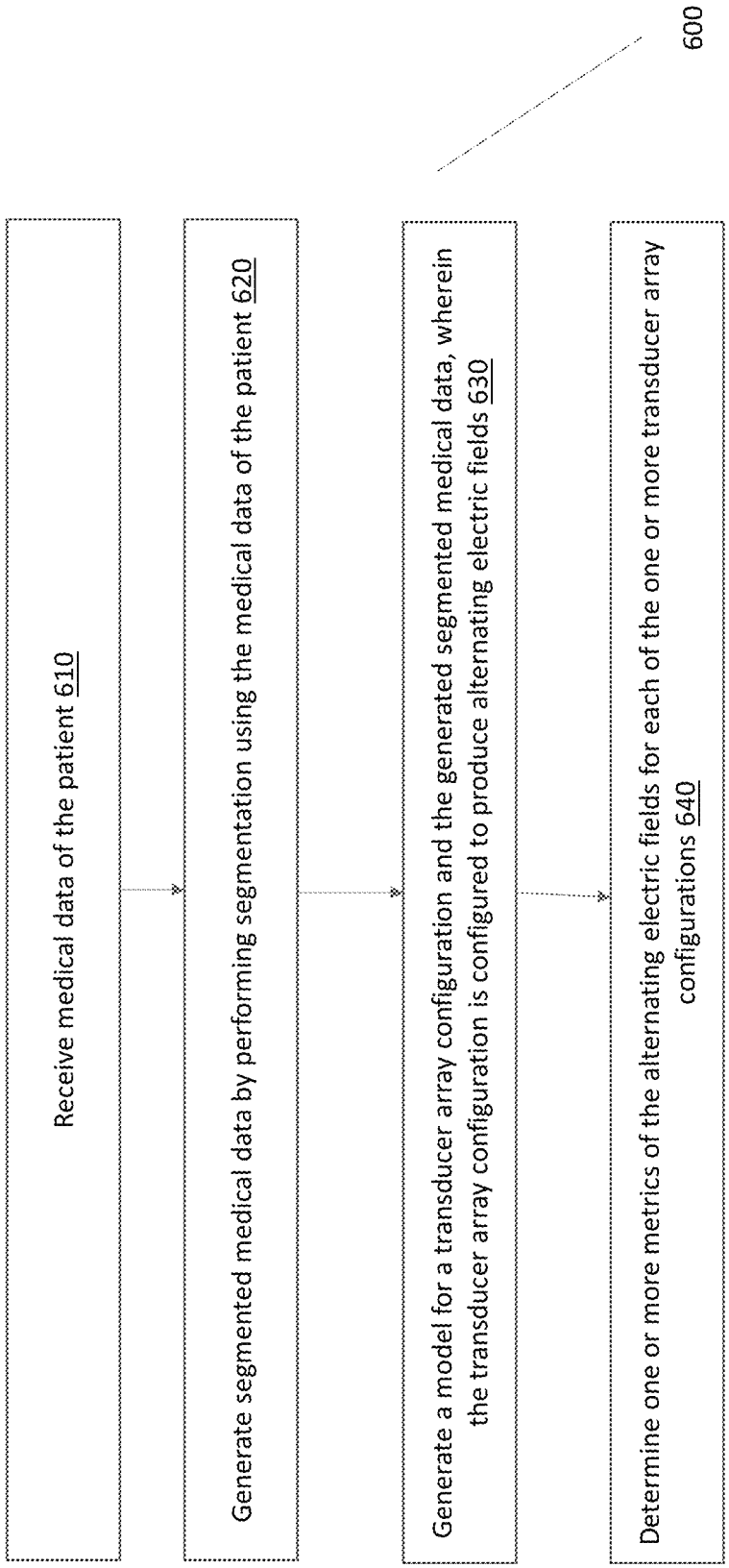
FIG. 6 is a flow diagram showing steps of a method for performing finite element analysis of alternating electric fields, in accordance with certain embodiments described herein.

FIG. 6 is a flow diagram showing steps of a method 600 for performing finite element analysis of alternating electric fields, in accordance with certain embodiments described herein.

In step 610, a system, such as system 100 of FIG. 1, may be configured to receive medical data of the patient. In step 620, the system may generate segmented medical data by performing segmentation using the medical data of the patient. In step 630, the system may generate a model for a transducer array configuration and the generated segmented medical data, wherein the transducer array configuration is configured to produce alternating electric fields. In step 640, the system may determine one or more metrics of the alternating electric fields for each of the one or more transducer array configurations. For example, the metrics can be any of the metrics described herein, or any suitable metric.

Additionally, the method 600 may include the step of comparing the metrics to reference values and/or metrics of another transducer array configuration. The method 600 may additionally include the step of determining and/or recommending a best or optimal transducer array configuration, for example, the system may be configured to recommend a transducer array configuration having a maximum value of a metric, or a minimum value of a metric, or a maximum or minimum value of a function of the metrics.

Figure 7:
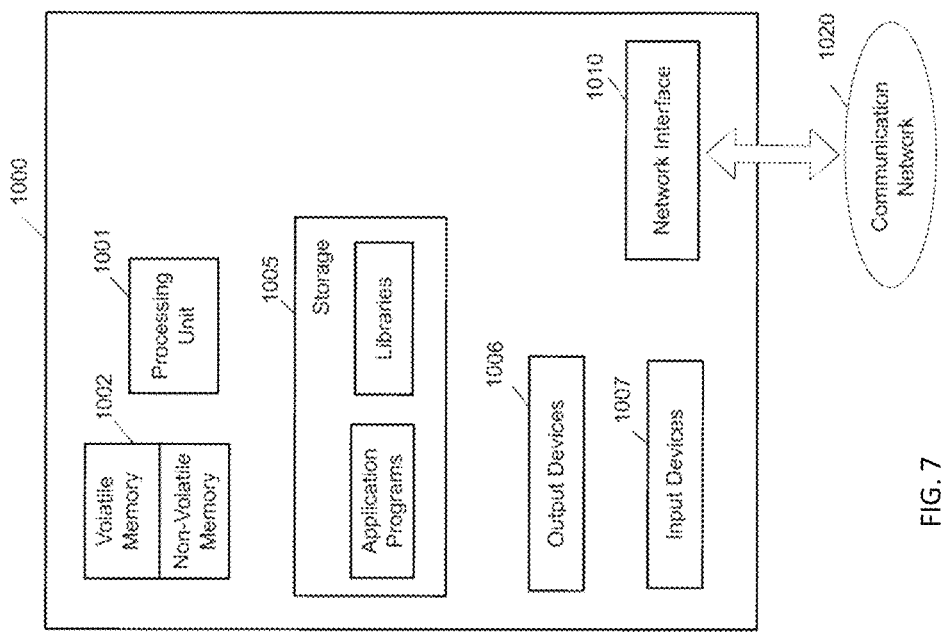
FIG. 7 shows, schematically, an illustrative computer 1000 on which any aspect of the present disclosure may be implemented.

FIG. 7 shows, schematically, an illustrative computer 1000 on which any aspect of the present disclosure may be implemented. In the example shown in FIG. 7, the computer 1000 includes a processing unit 1001 having one or more processors and a computer-readable storage medium 1002 that may include, for example, volatile and/or non-volatile memory. The memory 1002 may store one or more instructions to program the processing unit 1001 to perform any of the functions described herein. The computer 1000 may also include other types of computer-readable medium, such as storage 1005 (e.g., one or more disk drives) in addition to the system memory 1002. The storage 1005 may store one or more application programs and/or resources used by application programs (e.g., software libraries), which may be loaded into the memory 1002.

The computer 1000 may have one or more input devices and/or output devices, such as output devices 1006 and input devices 1007 illustrated in FIG. 7. These devices may be used, for instance, to present a user interface. Examples of output devices that may be used to provide a user interface include printers, display screens, and other devices for visual output, speakers and other devices for audible output, braille displays and other devices for haptic output, etc. Examples of input devices that may be used for a user interface include keyboards, pointing devices (e.g., mice, touch pads, and digitizing tablets), microphones, etc. For instance, the input devices 1007 may include a microphone for capturing audio signals, and the output devices 1006 may include a display screen for visually rendering, and/or a speaker for audibly rendering, recognized text.

In the example of FIG. 7, the computer 1000 may also include one or more network interfaces (e.g., network interface 1010) to enable communication via various networks (e.g., communication network 1020). Examples of networks include local area networks (e.g., an enterprise network), wide area networks (e.g., the Internet), etc. Such networks may be based on any suitable technology, and may operate according to any suitable protocol. For instance, such networks may include wireless networks and/or wired networks (e.g., fiber optic networks).

Results

Figure 5:
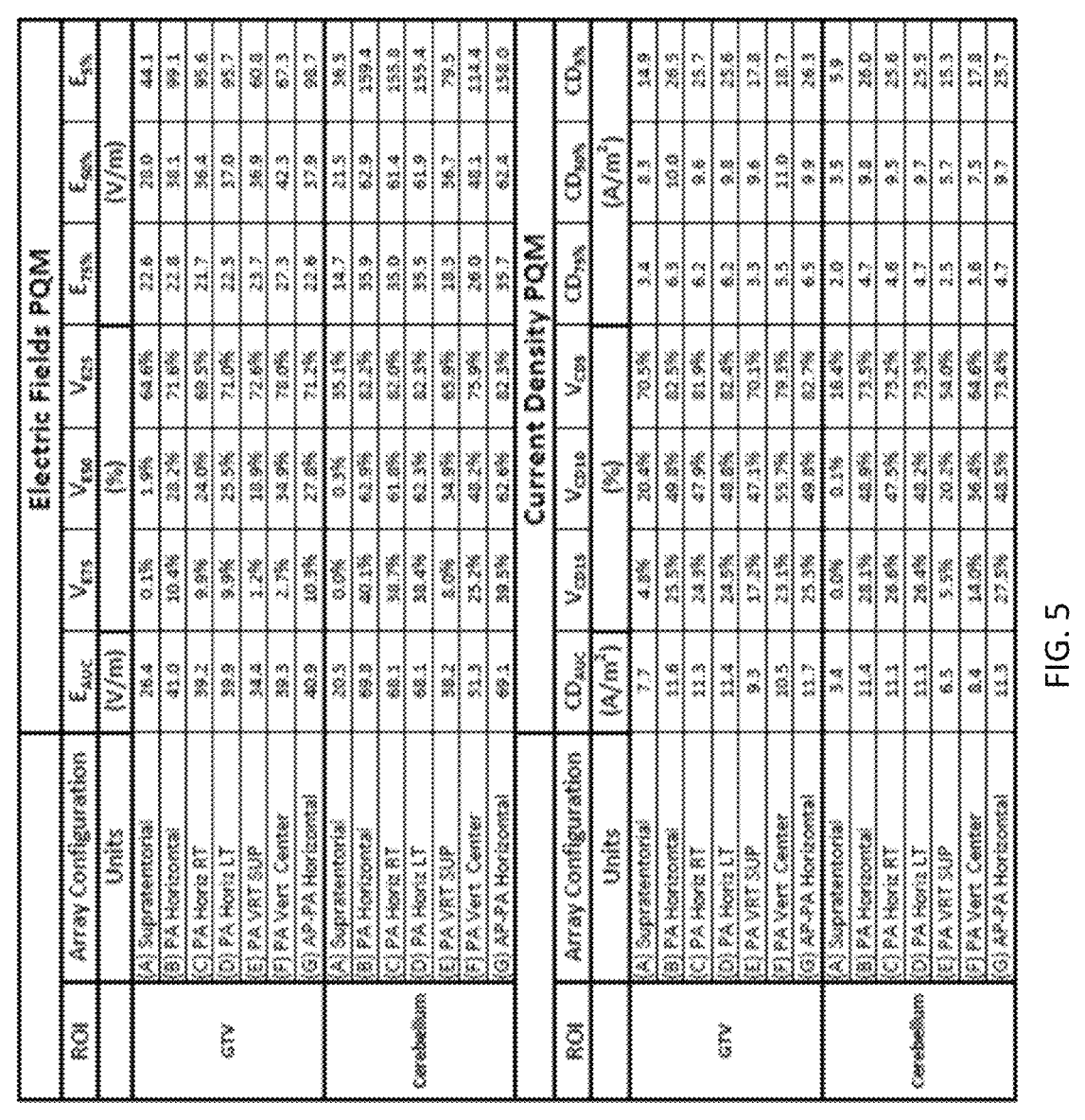

The example provided in FIGS. 2-5 show that array positioning greatly affects TTFields coverage of the GTV in the posterior fossa. For example, FIG. 5 is a table with values of metrics from performing finite element analysis using the patient medical data and configurations provided in FIG. 2.

The posterior fossa configurations consist of posterior displacement of the 2 lateral opposing arrays and the PA array, resulting in an average increase of 48.0% in $E_{AUC}$ and 41.9% in $CD_{AUC}$ at the GTV when compared to the supratentorial array configuration, as shown in FIG. 5. Since the GTV was located dorsally at the midline, and patients are routinely required to shift their arrays by 2 cm laterally during array exchange in order to reduce the amount of scalp erythema, one contemplation included whether or not lateral and superior shifts, as well as rotations of the PA array (which was closest to the GTV), would have a profound effect on TTFields coverage at the GTV.

As can be seen by FIG. 5, out of all of the alternative array configurations in this study, the configuration with the least electric field coverage to the GTV when compared to the supratentorial array configuration, was the PAVertical-Superior configuration 250. The overall field intensity of this alternative configuration yielded an $E_{AUC}$ of 34.4 V/m versus 26.4 V/m for the supratentorial array configuration, as can be seen in the graph 410 and in FIG. 5, or a 30.1% increase. The PAVertical-Superior array configuration also produced a median electric field intensity E50% of 36.9 V/m vs 28.0 V/m (graph 410 and in FIG. 5), or a 31.9% increase, and a CDAUC of 9.3 A/m2 versus 7.7 A/m2 (graph 420 and in FIG. 5), or a 20.3% increase. Interestingly, the median CD50% of the GTV for both PAVertical-Superior and PAHorizontal-RT array configurations was similar, 9.6 versus 8.3 A/m2 (graph 420 and in FIG. 5), or a 15.9% increase in median current density.

In contrast, of the 6 alternative array configurations modeled, the arrangement that provided the largest increase in field coverage at the GTV was observed when the PA array was positioned centrally along the patient's posterior neck and horizontally parallel, along the longer axis of the array, to the axial plane of the head, or the PAHorizontal configuration 220. This configuration yielded an $E_{AUC}$ of 41.0 versus an $E_{AUC}$ of 26.4 V/m in the supratentorial configuration (graph 410 and in FIG. 5), or a 55.2% increase in overall electric field coverage. Similarly, this configuration produced a 36.3% increase in E50%, 38.1 versus 28.0 V/m (graph 410 and in FIG. 5), respectively. Interestingly, the highest median electric field intensity within the GTV (42.3 V/m) was observed in the PAVertical-Center configuration. Likewise, the PAHorizontal configuration had a 50.3% increase in overall current density $CD_{AUC}$ when compared to the supratentorial configuration, 11.6 versus 7.7 A/m2 (graph 420 and in FIG. 5) respectively. The CD50% for the PAHorizontal configuration was 10.0 A/m2 while the CD50% for the supratentorial configuration was 8.3 A/m2 (graph 420 and in FIG. 5), or a 20.5% increase in median current density coverage to the GTV. Interestingly, the PAVertical-Center configuration also produced the highest median current density of 11.0 A/m2 in the GTV (graph 420 and in FIG. 5).

The AP array is complementary to the PAHorizontal array and therefore the AP array position may alter the electric field and current density. To investigate this, one experiment included rotating the AP array by 90 degrees in the AP-PAHorizontal array configuration and solved for various electric field and current density parameters in the model. Both AP-PAHorizontal and PAHorizontal configurations had comparable $E_{AUC}$ metrics, 40.9 V/m versus 41.0 V/m respectively or a difference of 0.4%, and E50% metrics, 37.9 versus 38.1 V/m respectively or a difference of 0.5% (graph 410 and in FIG. 5). Similarly, both configurations had comparable $CD_{AUC}$ metrics, 11.7 A/m2 versus 11.6 A/m2 respectively or a difference of 0.4%, and CD50% metrics, 9.9 A/m2 versus 10.0 A/m2 respectively or a difference of 0.1% (graph 420 and in FIG. 5). Other alternative array configurations yielded comparable electric field and current density coverage. Collectively, the computer simulation data indicate that the posterior fossa configuration provided improved electric field delivery to the patient's cerebellar glioblastoma compared to the standard supratentorial configuration.

Hotspots are generally regions or a percentage volume of a particular ROI that receives a greater quantity than that prescribed. Since TTFields do not currently have a clinically relevant threshold dose, 5% of the ROI receiving the highest TTFields intensity was chosen as the percentage volume representing a hotspot within that ROI and this is denoted as the E5%. The average electric field hotspot within the GTV was 44.1 V/m using the supratentorial array configuration while the average for the alternative array configurations was 86.2 V/m, or an average increase of 95.6%. Hotspots are proportional to TTFields coverage of the GTV in the posterior fossa.

The alternative array configuration with the lowest hotspot intensity within the GTV was PAVertical-Superior, with E5% of 60.8 V/m compared to 44.1 V/m from the supratentorial configuration (410 and FIG. 5), respectively, or a 38.1% increase. In contrast, the alternative array configuration with the highest hotspot intensity within the GTV was the PAHorizontal configuration with E5% of 99.1 V/m compared to 44.1 V/m from the supratentorial configuration (410 and FIG. 5), respectively, or a 125.0% increase.

The example provided in FIGS. 2-5 show that array positioning significantly alters TTFields coverage within the cerebellum.

Although the ROI for TTFields therapy is the GTV, it is also informative to observe and compare differences in TTFields distribution within adjacent normal tissue structures such as the cerebellum in this particular study. With an $E_{AUC}$ of 20.5 V/m in the supratentorial array configuration, the average $E_{AUC}$ for the alternative array configurations in aggregate was 60.8 V/m (430 and FIG. 5), or a 197.1% increase. The median electric field within the cerebellum for the supratentorial configuration yielded an E50% of 21.5 V/m compared to an E50% of 36.7 V/m, or 70.7% increase, for the PAVertical-Superior and an E50% of 62.9 V/m, or 192.6% increase, for the PAHorizontal configuration, which were the alternative array configurations with the smallest and largest field intensity change, respectively (430 and FIG.

5). Similarly, the supratentorial array configuration produced a $CD_{AUC}$ of 3.4 A/m2 while the average $CD_{AUC}$ in the alternative array configurations was 10.0 A/m2 (440 and FIG. 5), or a 192.6% increase on average. The alternative array configuration with the smallest median current density was the PAVertical-Superior with a CD50% of 5.7 A/m2 while the PAHorizontal array configuration yielded the largest median current density of CD50% of 9.8 A/m2, compared to a CD50% of 3.5 A/m2 for the supratentorial array configuration (440 and FIG. 5), or a 61.4% increase versus a 176.1% increase, respectively.

Electric field hotspots in the cerebellum measured by the E5% was 36.5 V/m for the supratentorial array configuration while the E5% for PAVertical-Superior was 79.5 V/m, or a 117.6% increase, and the E5% for PAHorizontal was 159.4 V/m, or a 336.3% increase (430 and FIG. 5).

Similarly, current density hotspots within the cerebellum measured by the CD5% was 5.9 A/m2 for the supratentorial array configuration while the CD5% was 15.3 A/m2, or a 157.3% increase, and 26.0 A/m2, or a 338.2% increase, for the PAVertical-Superior and the PAHorizontal posterior fossa array configurations, respectively (440 and FIG. 5).

Discussion

TTFields therapy is an accepted treatment modality for patients with glioblastoma and a better understanding is needed on array positioning that can affect TTFields coverage at the tumor target. This is particularly important for glioblastomas located within the posterior fossa and, to the knowledge of the inventors, the data provided herein is the first to show that the standard array configuration does not provide adequate electric field coverage for the GTV located in this region. However, the alternative array configurations for the posterior fossa provided an average of 48.0% more coverage to the GTV as measured by the $E_{AUC}$. In addition, hotspots defined by the E5% had an average increase as much as 95.6%. Although only 4% of adult gliomas are located in the posterior fossa and the biology of these tumors is probably different from those located in the supratentorial brain, posterior fossa glioblastomas may still benefit from TTFields. This is because the mechanism of TTFields' anti-tumor effect applies to any dividing tumor cells where large proteins with high dipole moments are required for cytokinesis and segregation of sister chromatids during metaphase and anaphase in mitosis. With specific placement of the arrays as part of treatment planning, TTFields can potentially become a precision-guided anti-tumor therapy targeting dividing glioblastoma cells at a pre-specified location in the brain. Therefore, determining the electric field coverage of the glioblastoma within the intracranial space is highly relevant to patient care.

Array positioning has been shown to affect the electric field strength at various intracranial structures and particularly at the GTV. To quantify this effect, a set of PQM parameters derived from the EVH and CDVH of different models was used. PQM has been used to evaluate treatment plans to ensure adequate coverage to the target(s) while minimizing doses to the surrounding normal tissue. For the application in TTFields, relevant parameters include EAUC and CDVHAUC for an aggregate measure of electric field and current density coverage at the GTV, as well as measurements of E5% and CDVH5% at hotspots within the GTV, respectively. Indeed, using this method, a user can compare quantitatively the strength of the electric fields and current densities across a number of array configurations.

A similar analysis including computing TTFields intensity and power distribution for supratentorial glioblastomas was performed utilizing MRI data from subjects participated in the EF-14 randomized clinical trial. Using a parameter of local minimum dose density at the GTV, which is defined as the product of TTFields intensity, tissue-specific conductivities and patient compliance, a correlation was found between dose density and survival. However, only 340 (73%) of the entire TTFields-treated population (n=466) had MRI qualities acceptable for analysis and the outcome of this analysis remains to be confirmed in a validation cohort.

The finite element analysis revealed that TTFields coverage of the cerebellar glioblastoma was greatly improved with any of the alternative array configurations for the posterior fossa when compared to the standard supratentorial configuration. This is most likely due to the increased proximity of the PA array to the tumor, which is located at the dorsal region of the posterior fossa. Of the 6 alternative configurations 220, 230, 240, 250, 260 and 270, the PAHorizontal array configuration provided the most extensive coverage to the GTV. This benefit is most likely attributed to coverage of the entire GTV with increased electric fields provided by the PA array. Specifically, the PAhorizontal configuration, in comparison to the PAVertical-Superior and PAVertical-Center configurations, decreases the distance between the PA and the two lateral arrays, and therefore increases the electric field intensity within the posterior fossa. This increase in field strength has been observed by other studies performing similar TTFields modeling. A probable and additional attribution to the increased coverage could be due to the slight angular rotation and posterior shift of the right and left lateral arrays, providing a higher current density throughout the posterior portion of the brain and thereby increasing electric field coverage to the GTV.

By applying the fields to the head using the PAHorizontal configuration, the computer modeling revealed a qualitative increase in the electric field penetration at the GTV, compared to the PAVertical-Superior and PAVertical-Center configurations, when the PA array was rotated so that the long axis of the array was parallel to the coronal plane. However, this array position also increased the field intensity within the vertebral bodies and muscles posteriorly in the neck. As shown in overlays 320 to 340, the three horizontal PA configurations produced higher field intensities at the odontoid of the C2 vertebral body when compared to the PAVertical-Superior and PAVertical-Center configurations, and even more so when compared to the supratentorial configuration. In addition, a qualitative assessment of models applying the PAHorizontal, PAHorizontal-RT and PAHorizontal-LT configurations produced an increase in field intensity within the scalp region inferiorly but a decrease in field intensity superiorly. When shifted laterally left or right by 2 cm from the PAHorizontal configuration, only marginal and probably non-clinically relevant differences in field coverage of the GTV were observed. Additionally, by rotating the AP array by 90 degrees in the AP-PAHorizontal configuration, only marginal differences were observed in fields coverage quantified by the various PQM metrics. This suggests that rotating the AP array, potentially provides another means of applying roughly the same field intensity as the PAHorizontal configuration for tumors in the posterior fossa.

An increase in the electric field intensity was also observed at the genu of the corpus callosum and the anterior one-third of the body of this structure in the alternative array configurations. This is likely due to the fact that the most inferior margin of the fields extends well beyond the posterior commissure line and thus TTFields cover a greater area of the corpus callosum. However, in the supratentorial array configuration, the margin of the field only tangentially skims the posterior commissure line.

Finite element modeling may depend on experimentally measured electric field data for both supratentorial and alternative array configurations in the posterior fossa, which may be obtained from clinical trials in which the electric field intensity is measured in the patient while TTFields are being applied to the scalp. Finite element modeling may also depend on the conductivity and permittivity values for glioblastoma, which may be obtained from experimental measurements. Prior sensitivity analysis has shown that the electric field strength from modeling is primarily influenced by tissue conductivity rather than permittivity.

In summary, this is the first finite element modeling of a cerebellar glioblastoma and the data shows that the alternative array configuration for the posterior fossa offers an improved TTFields coverage to the tumor compared to the conventional supratentorial array configuration. This increased electric field coverage is due to shifting of the PA array to the lower occipital and upper cervical regions while the right and left lateral arrays are moved backward. Benefit of this array positioning will require clinical validation.

While the above description has described various circuitry and methods for operating such circuitry in the context of ultrasound devices, the circuitry and methods may be used in the context of other electronic devices as well.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. A compute-implemented method for determining a transducer array configuration for a patient, the method comprising:
    generating, by a computer system, segmented medical data by performing segmentation on medical data of the patient, the medical data comprising data on a gross tumor volume (GTV) of the patient;
    generating, by the computer system, for each of a plurality of transducer array configurations, a model for the transducer array configuration and the segmented medical data, wherein each of the transducer array configurations is configured to produce alternating electric fields;
    determining, by the computer system, based on the models, metrics of the alternating electric fields for each of the transducer array configurations; and
    determining, by the computer system, based on a function of the metrics of the alternating electric fields for each of the transducer array configurations, a recommended transducer array configuration for the GTV of the patient.

2. The method of claim 1, further comprising generating, by the computer system, an electric field-volume histogram (EVH) and/or a current density volume histogram (CDVH).

3. The method of claim 2, wherein the metrics comprise an area under a curve in the EVH ($E_{AUC}$) and/or an area under a curve in the CDVH ($CD_{AUC}$).

4. The method of claim 1, wherein the metrics are indicative of strengths of the alternating electric fields and current densities of the alternating electric fields.

5. The method of claim 1, wherein the metrics comprise Plan Quality Metrics (PQM).

6. The method of claim 1, wherein the alternating electric fields comprise tumor treating fields (TTFields).

7. The method of claim 1, wherein the metrics comprise a median volume for the alternating electric fields covering the patient's GTV and cerebellum.

8. The method of claim 1, wherein the determining of the recommended transducer array configuration comprises comparing, by the computer system, the metrics of each of the transducer array configurations.

9. The method of claim 1, wherein the metrics comprise an average electric field hotspot.

10. The method of claim 1, wherein the model comprises a three-dimensional finite-element mesh.

11. The method of claim 1, wherein the determining of the metrics comprises performing finite element analysis.

12. The method of claim 1, wherein the performing of the segmentation comprises segmenting neuro-anatomical structures.

13. The method of claim 1, wherein the medical data includes T1 and/or T2 MRI sequences.

14. A system, comprising:
  at least one computer hardware processor; and
  at least one non-transitory computer-readable storage medium storing processor-executable instructions that, when executed by the at least one computer hardware processor, cause the at least one computer hardware processor to perform a computer-implemented method for determining a transducer array configuration for a patient, the method comprising:
    generating segmented medical data by performing segmentation on medical data of the patient, the medical data comprising data on a gross tumor volume (GTV) of the patient;
    generating, for each of a plurality of transducer array configurations, a model for the transducer array configuration and the segmented medical data, wherein each of the transducer array configurations is configured to produce alternating electric fields;
    determining, based on the models, metrics of the alternating electric fields for each of the transducer array configurations; and
    determining, based on a function of the metrics of the alternating electric fields for each of the transducer array configurations, a recommended transducer array configuration for the GTV of the patient.

15. The system of claim 14, wherein the method further comprises generating an electric field-volume histogram (EVH) and/or a current density volume histogram (CDVH).

16. The system of claim 15, wherein the metrics comprise an area under a curve in the EVH ($E_{AUC}$) and/or an area under a curve in the CDVH ($CD_{AUC}$).

17. The system of claim 14, wherein the metrics are indicative of strengths of the alternating electric fields and current densities of the alternating electric fields.

18. The system of claim 14, wherein the metrics comprise Plan Quality Metrics (PQM).

19. The system of claim 14, wherein the metrics comprise any one or any combination of:
  a median volume for the alternating electric fields covering the patient's GTV and cerebellum, and
  an average electric field hotspot.

20. The system of claim 14, wherein the determining of the recommended transducer array configuration comprises comparing the metrics of each of the transducer array configurations.

* * * * *

UNITED STATES PATENT AND TRADEMARK OFFICE
CERTIFICATE OF CORRECTION

| | | |
|---|---|---|
| PATENT NO. | : 11,869,151 B2 | Page 1 of 1 |
| APPLICATION NO. | : 17/585187 | |
| DATED | : January 9, 2024 | |
| INVENTOR(S) | : Eric T. Wong et al. | |

It is certified that error appears in the above-identified patent and that said Letters Patent is hereby corrected as shown below:

In the Claims

At Column 12, Claim 1, Line 21, the text "1. A compute-implemented method for determining a" should read -- 1. A computer-implemented method for determining a --.

At Column 13, Claim 14, Line 12, the text "processor to perform a compute,:implemented method" should read -- processor to perform a computer-implemented method --.

Signed and Sealed this
Ninth Day of April, 2024

*Katherine Kelly Vidal*

Katherine Kelly Vidal
*Director of the United States Patent and Trademark Office*